US012569219B2

(12) United States Patent
Allaire et al.

(10) Patent No.: US 12,569,219 B2
(45) Date of Patent: Mar. 10, 2026

(54) METHODS AND SYSTEMS FOR VALVE REGURGITATION ASSESSMENT

(71) Applicant: KONINKLIJKE PHILIPS N.V., Eindhoven (NL)

(72) Inventors: Stéphane Allaire, Nanterre (FR); Odile Bonnefous, Rueil-Malmaison (FR); Helene Langet, Buc (FR); Scott William Dianis, Andover, MA (US); Jimmy Li-Shin Su, Arlington, MA (US); Qifeng Wei, Wayland, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 377 days.

(21) Appl. No.: 17/423,892

(22) PCT Filed: Feb. 4, 2020

(86) PCT No.: PCT/EP2020/052667
§ 371 (c)(1),
(2) Date: Jul. 18, 2021

(87) PCT Pub. No.: WO2020/164955
PCT Pub. Date: Aug. 20, 2020

(65) Prior Publication Data
US 2022/0079551 A1     Mar. 17, 2022

(30) Foreign Application Priority Data
Feb. 11, 2019     (EP) .................................... 19290010

(51) Int. Cl.
A61B 8/06        (2006.01)
A61B 8/00        (2006.01)
A61B 8/08        (2006.01)

(52) U.S. Cl.
CPC .............. *A61B 8/06* (2013.01); *A61B 8/0883* (2013.01); *A61B 8/469* (2013.01); *A61B 8/5246* (2013.01); *A61B 8/5261* (2013.01)

(58) Field of Classification Search
CPC ......... A61B 8/06; A61B 8/0883; A61B 8/469; A61B 8/5246; A61B 8/5261
See application file for complete search history.

(56) References Cited

U.S. PATENT DOCUMENTS 5,997,479 A     12/1999  Savord
6,013,032 A      1/2000  Savord
(Continued)

OTHER PUBLICATIONS

O. Somphone et al, Fast myocardial motion and strain estimation in 3D cardiac ultrasound with sparse demons, in proceedings of ISBI '13 pp. 1182-1185 (2013) (Year: 2013).*
(Continued)

*Primary Examiner* — Pascal M Bui Pho
*Assistant Examiner* — Nicholas A Robinson

(57) ABSTRACT

The invention provides a method for assessing cardiac valve regurgitation. The method includes obtaining 4D ultrasound data of a region of interest, wherein the region of interest comprises a cardiac valve. The 4D ultrasound data comprises a time sequence of 3D ultrasound images comprising B-mode ultrasound data and color Doppler ultrasound data. Image stabilization is performed on the images of the time sequence of 3D ultrasound images and a dynamic jet is then segmented from the time sequence of stabilized 3D ultrasound images. A dynamic surface model is fit to the valve in the time sequence of stabilized 3D ultrasound images based on the segmented jet. The method further includes identifying a dynamic regurgitant orifice based on the applied surface model and the time sequence of stabilized 3D ultrasound images and fitting a flow convergence model to the time sequence of stabilized 3D ultrasound images based (Continued)

on the identified dynamic regurgitant orifice. A regurgitant flow is then estimated based on the identified regurgitant orifice.

20 Claims, 4 Drawing Sheets

(56) References Cited

U.S. PATENT DOCUMENTS

| | | | |
|---|---|---|---|
| 6,283,919 B1 | 9/2001 | Roundhill | |
| 6,443,896 B1 | 9/2002 | Detmer | |
| 6,458,083 B1 | 10/2002 | Jago | |
| 6,623,432 B2 | 9/2003 | Powers | |
| 2003/0114750 A1* | 6/2003 | Brock-Fisher | A61B 8/06 |
| | | | 600/431 |
| 2004/0019278 A1* | 1/2004 | Abend | G01S 7/52061 |
| | | | 600/454 |
| 2005/0124885 A1* | 6/2005 | Abend | A61B 8/085 |
| | | | 600/443 |
| 2008/0097204 A1* | 4/2008 | Thiele | G01S 15/8993 |
| | | | 600/437 |
| 2011/0208056 A1 | 8/2011 | Datta | |
| 2013/0261457 A1 | 10/2013 | Wei | |
| 2014/0052001 A1* | 2/2014 | Ionasec | A61B 5/7264 |
| | | | 600/440 |
| 2015/0025666 A1* | 1/2015 | Olivieri | G06F 30/00 |
| | | | 700/98 |
| 2015/0148679 A1* | 5/2015 | Thiele | G01S 15/8979 |
| | | | 600/454 |
| 2015/0366532 A1* | 12/2015 | Voigt | A61B 8/488 |
| | | | 600/408 |
| 2016/0217570 A1* | 7/2016 | Schadewaldt | G06T 7/149 |

OTHER PUBLICATIONS

O. Somphone et al, Live feature tracking in ultrasound liver sequences with sparse demons, in proceedings of MICCAI'14 workshop: Challenge on Liver Ultrasound Tracking (2014) (Year: 2014).*

Siefert AW, Icenogle DA, Rabbah JP, Saikrishnan N, Rossignac J, Lerakis S, Yoganathan AP. Accuracy of a mitral valve segmentation method using J-splines for real-time 3D echocardiography data. Ann Biomed Eng. Jun. 2013;41(6):1258-68. doi:10.1007/s10439-013-0784-8. Epub Mar. 5, 2013. PMID: 23460042; (Year: 2013).*

International Search Report and Written Opinion of PCT/EP2020/052667, dated Apr. 29, 2020.

Wang, Yang et al "Automatic Detection and Quantification of Mitral regurgitation on TTE with Application to Assist Mitral Clip Planning and Evaluation", Clinical Image-Based Procedures. From Planning to Intervention, Oct. 2012.

Somphone, O. et al "Fast Myocardial Motion and Strain Estimation in 3D Cardiac Ultrasound with Saprse Demons", Proceedings of ISBI, 2013, pp. 1182-1185.

Somphone, O. et al "Live Feature Tracking in Ultrasound Liver Sequences with Sparse Demons", Proceedings of MICCAI, 2014 Workshop: Challenge on Liver Ultrasound tracking.

De Simone, R. et al "Three-Dimensional Doppler", European Heart Journal, vol. 20, 1999, pp. 619-627.

Son, Jang-Won et al "Automated Quantification of Mitral Regurgitation by Three Dimensional Real Time Full Volume Color Doppler Transthoracic Echocardiography: A Validation with Cardiac Magnetic Resonance Imaging and Comparison with Two Dimensional Quantitative Methods", Journal Cardiovascular Ultrasound, vol. 21, No. 2, 2013, pp. 81-89.

Thavendiranathan, Paaladinesh et al "Quantification of Chronic Functional Mitral Regurgitation by Automated 3-Dimensional Peak and Integrated Proximal Isovelocity Surface Area and Stroke Volume Techniques Using Real-Time 3-Dimensional Volume Color Doppler Echocardiography In Vitro and Clinical Validation", Circular Cardiovascular Imaging, vol. 6, 2013, pp. 125-133.

* cited by examiner

Obtain 4D U/S    110

Stabilize Image    120

Segment Dynamic Jet    130

Fit Surface Model    140

Identify Regurgitant Orifice    150

Fit Convergence Model    160

Estimate Regurgitant Flow    170

100

270

METHODS AND SYSTEMS FOR VALVE REGURGITATION ASSESSMENT

CROSS-REFERENCE TO PRIOR APPLICATIONS

This application is the U.S. National Phase application under 35 U.S.C. § 371 of International Application No. PCT/EP2020/052667, filed on Feb. 4, 2020, which claims the benefit of European Patent Application No. 19290010.8, filed on Feb. 11, 2019. These applications are hereby incorporated by reference herein.

FIELD OF THE INVENTION

The invention relates to the field of ultrasound, and more specifically to the field of ultrasound imaging for assessing valve regurgitation.

BACKGROUND OF THE INVENTION

Regurgitation, such as mitral regurgitation, relates to leaking heart valves. Sometimes the condition is minor and may not require treatment, but other times valve regurgitation places a strain on the heart. It can cause the heart to work harder and it may not pump the same amount of blood. It is well known that it is desirable to detect valve regurgitation.

Proximal isovelocity surface area (PISA) measurement, also known as the "flow convergence" method, can be used in echocardiography to estimate the area of an orifice through which blood flows. The PISA method has for example been applied clinically to the evaluation of mitral regurgitation (MR), mitral stenosis and tricuspid regurgitation The PISA method determines a regurgitant volume (RV). It is the recommended method for assessing mitral valve regurgitation (MR) severity, and makes use of transthoracic (TTE) and transesophageal (TEE) echocardiography. However, 2D-based MR quantification by the 2D PISA method relies on various geometric assumptions, such as a hemispheric flow convergence shape, a circular orifice and a central regurgitant jet. These assumptions limit the reliability and accuracy of assessments made beyond the simplest MR mechanisms. In addition, 2D PISA RV has been found to present poor agreement with RV derived from cardiac magnetic resonance imaging (cMRI), which is a more accurate but resource intensive method.

There is therefore a need for a method for assessing a regurgitant valve in a robust and accurate manner, without requiring significant additional hardware.

Yang Wang et al: "Automatic Detection and Quantification of Mitral Regurgitation on TTE with Application to Assist Mitral Clip Planning and Evaluation" 5 Oct. 2012, CLINICAL IMAGE-BASED PROCEDURES. FROM PLANNING TO INTERVAENTION, SPRINGER BERLIN HEIDELBERG, BERLIN, HEIDELBERG, PAGES(S) 33-41, XP047027625 discloses a method to automatically locate and quantify mitral regurgitation.

US 2014/052001 discloses a method of automatically detecting and quantifying mitral regurgitation based on B-mode and Doppler ultrasound data acquired by TTE.

US 2015/366532 discloses a method for detecting a regurgitant orifice based on B-mode and Doppler ultrasound data.

SUMMARY OF THE INVENTION

The invention is defined by the claims.

According to examples in accordance with an aspect of the invention, there is provided a method for calculating cardiac valve regurgitation, the method comprising:

obtaining 4D ultrasound data of a region of interest, wherein the region of interest comprises a cardiac valve and wherein the 4D ultrasound data comprises a time sequence of 3D ultrasound images comprising B-mode ultrasound data and color Doppler ultrasound data;

performing image stabilization on the images of the time sequence of 3D ultrasound images;

segmenting a dynamic jet from the time sequence of stabilized 3D ultrasound images;

fitting a dynamic surface model to the valve in the time sequence of stabilized 3D ultrasound images based on the segmented dynamic jet;

identifying a dynamic regurgitant orifice based on the dynamic surface model and the time sequence of stabilized 3D ultrasound images;

fitting a flow convergence model to the time sequence of stabilized 3D ultrasound images based on the identified dynamic regurgitant orifice; and estimating a regurgitant flow based on the identified regurgitant orifice and time sequence of stabilized 3D ultrasound images.

The method provides an automated method for estimating the regurgitant flow of a valve.

The stabilization of each of the 3D ultrasound images provides for a stabilized view of the region of interest over the entire image sequence. The surface model may then be applied across the image sequence in order to identify any regurgitant flow from the orifice.

Image stabilization results in a sequence of stabilized B-mode images and stabilized color Doppler images on which subsequent image processing steps may be performed. For example, the image stabilization may reduce the disturbing motion of a heart valve during the cardiac cycle.

The 4D ultrasound data includes both B-mode ultrasound data and color Doppler ultrasound data. In this way, the 4D ultrasound data may contain structural data and blood flow data.

In an embodiment, the method further comprises receiving a user input, wherein the user input comprises one or more of:

selecting one or more 3D ultrasound image; and selecting an orifice within a 3D ultrasound image.

A user input may be used to assist the recognition of features within a 3D image or to select a given image for further investigation.

In an embodiment, performing the image stabilization comprises fast image stabilization.

In an arrangement, the fast image stabilization comprises applying a sparse optical flow method to the time sequence of stabilized 3D ultrasound images.

By employing a sparse optical flow method to the sequence of 3D ultrasound images, it is possible to quickly process the images. In this way, the method may be made more suitable for clinical applications and may handle real-time imaging applications.

In an embodiment, performing the image stabilization comprises applying a point selection routine to the time sequence of stabilized 3D ultrasound images.

In this way, a point selection routine may be used to identify common points within each of the 3D images, which may then be aligned based on identified common points.

In an arrangement, performing the image stabilization comprises performing a trajectory analysis on the time sequence of stabilized 3D ultrasound images, wherein the trajectory analysis comprises an anti-drifting mechanism.

In this way, it is possible to account for movement artefacts within the time sequence of stabilized 3D ultrasound images.

In an embodiment, segmenting the dynamic jet comprises averaging over the time sequence of stabilized 3D ultrasound images.

In a further embodiment, the averaging comprises averaging the shape of the dynamic jet over the time sequence of stabilized 3D ultrasound images.

In a further, or alternative, embodiment, the averaging comprises averaging the orientation of the dynamic jet over the time sequence of stabilized 3D ultrasound images.

In other words, the term averaging may refer to the averaging of the jet shape over time and/or the averaging over time of the estimated main direction of the jet.

In an embodiment, fitting the dynamic surface model comprises analytic geometric regression.

In an embodiment, the method further comprises estimating a regurgitant volume based on the estimated regurgitant flow.

According to examples in accordance with an aspect of the invention, there is provided a computer program comprising computer program code means which is adapted, when said computer program is run on a computer, to implement the method described above.

According to examples in accordance with an aspect of the invention, there is provided a processing unit, wherein the processing unit is adapted to:

obtain 4D ultrasound data of a region of interest, wherein the region of interest comprises a cardiac valve and wherein the 4D ultrasound data comprises a time sequence of 3D ultrasound images comprising B-mode ultrasound data and color Doppler ultrasound data;

perform fast image stabilization on the images of the time sequence of 3D ultrasound images;

segment a dynamic jet from the time sequence of stabilized 3D ultrasound images;

fit a dynamic surface model to the valve in the time sequence of stabilized 3D ultrasound images based on based on the segmented jet;

identify a dynamic regurgitant orifice based on the surface model and the time sequence of stabilized 3D ultrasound images;

fit a flow convergence model to the time sequence of stabilized 3D ultrasound images based on the identified dynamic regurgitant orifice; and estimate a regurgitant flow based on the identified regurgitant orifice and time sequence of stabilized 3D ultrasound images.

According to examples in accordance with an aspect of the invention, there is provided an ultrasound system, the system comprising:

a processing unit as claimed described above; and an ultrasound probe adapted to acquire the 4D ultrasound data.

In an embodiment, the system further comprises a user interface adapted to receive a user input.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
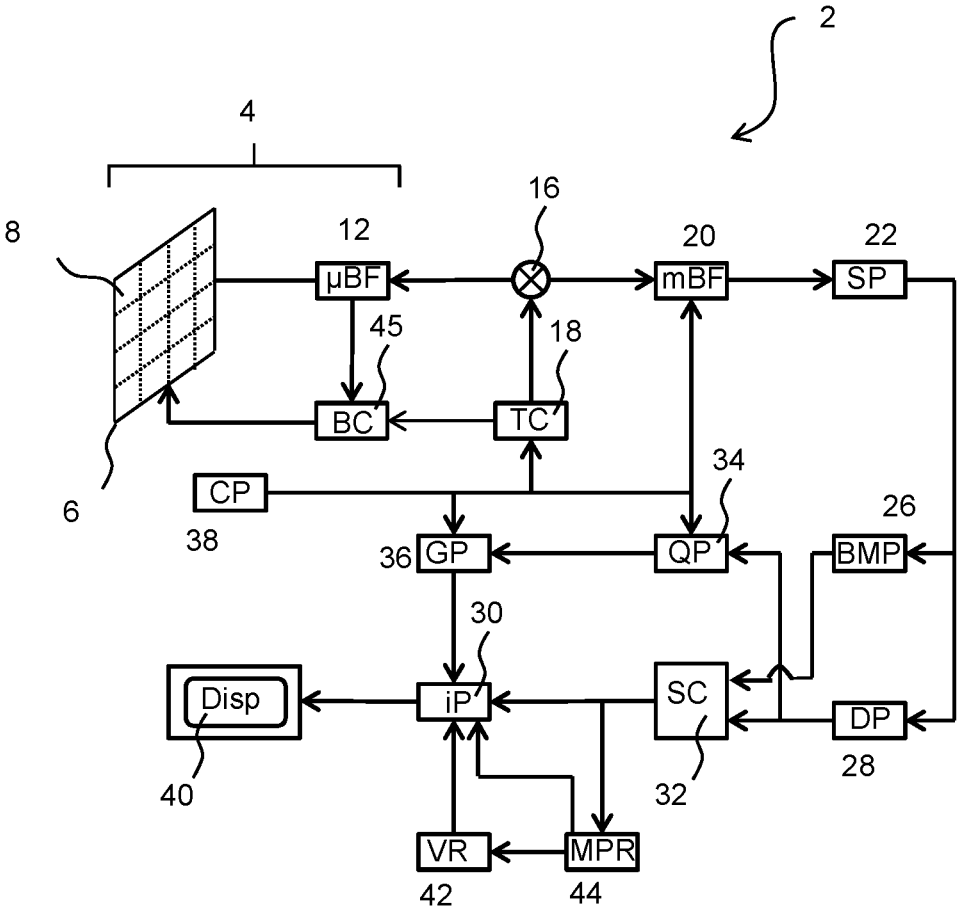
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for assessing cardiac valve regurgitation. The method includes obtaining 4D ultrasound data of a region of interest, wherein the region of interest comprises a cardiac valve. The 4D ultrasound data comprises a time sequence of 3D ultrasound images comprising B-mode ultrasound data and color Doppler ultrasound data. Image stabilization is performed on the images of the time sequence of 3D ultrasound images and a dynamic jet is then segmented from the time sequence of stabilized 3D ultrasound images. A dynamic surface model is fit to the valve in the time sequence of stabilized 3D ultrasound images based on the segmented jet. The method further includes identifying a dynamic regurgitant orifice based on the applied surface model and the time sequence of stabilized 3D ultrasound images and fitting a flow convergence model to the time sequence of stabilized 3D ultrasound images based on the identified dynamic regurgitant orifice. A regurgitant flow is then estimated based on the identified regurgitant orifice.

The general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of non-linear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

The methods described herein may be performed on a processing unit. Such a processing unit may be located within an ultrasound system, such as the system described above with reference to FIG. 1. For example, the image processor 30 described above may perform some, or all, of the method steps detailed below. Alternatively, the processing unit may be located in any suitable system, such as a monitoring system, that is adapted to receive an input relating to a subject.

The proposed automated 4D ultrasound processing method provides an improved reliability and accuracy for valve regurgitation assessment compared to the current clinical practice of 2D proximal isovelocity surface area assessment from 2D PISA transthoracic and transesophageal echographic sequences (TTE and TEE). Thus the limitations of typical 2D PISA methods, which rely on geometric assumptions are overcome. Furthermore, the proposed method improves the intra-observer and inter-observer reproducibility of the regurgitant volume quantification.

The invention allows the direct estimation of the regurgitant volume from orifice convergence data (similar to the 2D PISA principle, yet avoiding the geometric assumptions made in the 2D PISA method). Alternate solutions calculate the regurgitant volume indirectly by subtracting the left ventricle (LV) outflow from the LV inflow, which needs big enough a field of view to encompass the LV wall and the aortic valve.

In addition, the invention provides orifice segmentation over time. Furthermore, the invention provides the user with stabilized valve visualization and graphical segmentations and models, which further facilitate the understanding and visual assessment of the valve regurgitation.

Figure 2:
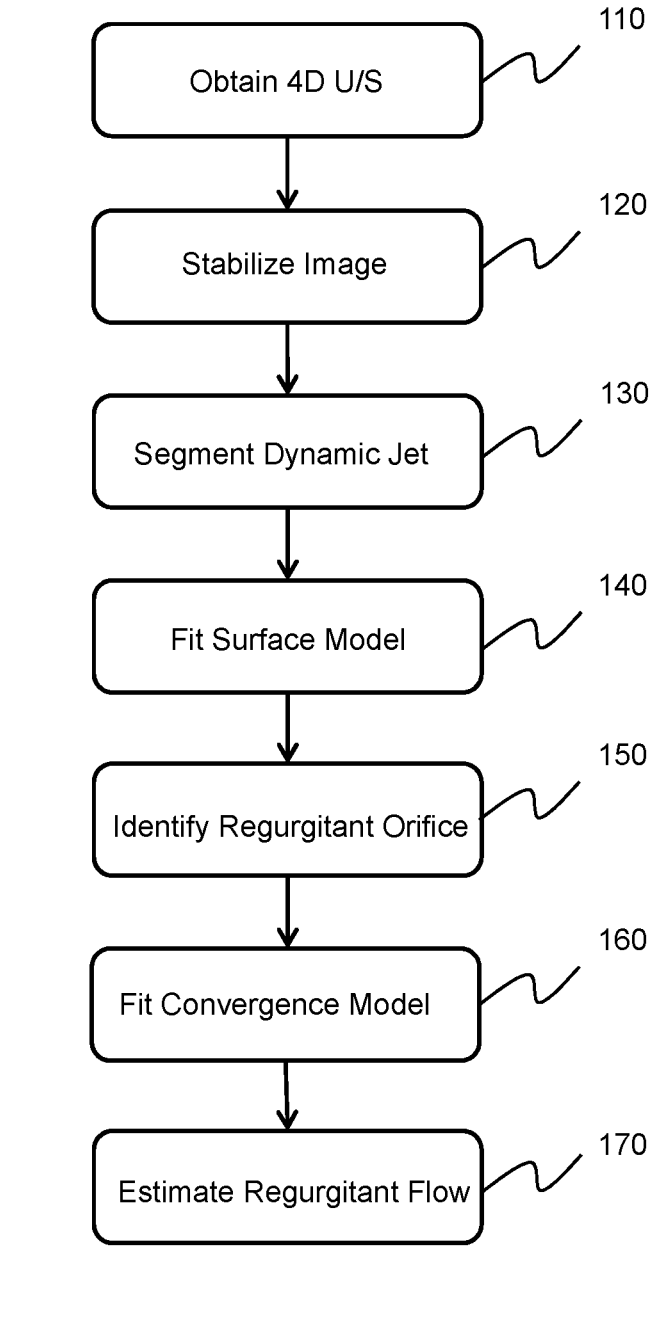
FIG. 2 shows a method of the invention.

FIG. 2 shows a method 100 for assessing cardiac valve regurgitation.

The method begins in step 110 by obtaining 4D ultrasound data of a region of interest. The region of interest comprises a cardiac valve to be investigated, which may be a valve of the heart of a subject. The valve may be a mitral valve or an aortic valve, for example.

The 4D ultrasound data comprises a time sequence of 3D ultrasound images. In other words, a time series of 3D ultrasound images showing a valve is acquired. Accordingly, a view of a given valve may be acquired across one or more cardiac cycles.

Various ultrasound modalities may be used to acquire the data. The 4D ultrasound data comprises both B-mode ultrasound data and color Doppler ultrasound data. The B-mode echo data and Doppler color data undergo scan conversion using classic geometric methods For example, 4D transesophageal echography (TEE) data and 4D transthoracic echography (TTE) data may be used.

In step 120, image stabilization is performed on the images of the time sequence of 3D ultrasound images of the 4D ultrasound data.

Performing image stabilization on the 4D ultrasound data provides a stabilized 3D time sequence of stabilized images, in B-mode and color Doppler data modes, which may then be used to obtain a stabilized visualization of a jet, a valve and/or an orifice.

The stabilization reduces, or eliminates, rigid translation motion (which may be referred to as shift or offset) which is estimated in the 4D B-mode ultrasound sequence. In addition, the stabilization reduces, or eliminates, the same motion in the 4D color Doppler ultrasound sequence, and in particular the cyclic movements of the cardiac valve in the heart, for example during the systolic phase for the mitral valve.

The image stabilization may be performed using a fast image stabilization method. In an example, the fast image stabilization may combine a sparse optical flow method for motion estimation as described in O. Somphone et al, Fast myocardial motion and strain estimation in 3D cardiac ultrasound with sparse demons, in *proceedings of ISBI '13* pp. 1182-1185 (2013).

Further, the image stabilization may employ a point selection routine and/or trajectory analysis methods with anti-drifting mechanisms similar to those described in O. Somphone et al, Live feature tracking in ultrasound liver sequences with sparse demons, in *proceedings of MIC-CAI'14 workshop: Challenge on Liver Ultrasound Tracking* (2014).

The point selection routine may be based around a given location, indicated by way of a user input. In other words, the method may further include receiving a user input. The user input may include selecting a 3D ultrasound image for further investigation. Further the user input may include selecting an orifice within a given 3D ultrasound image.

The user input may be received through any suitable user input device, such as a Graphical User Interface (GUI) that enables the user to select 3D frames of the 4D ultrasound data, for example where regurgitation occurs (where a jet appears), and click on an orifice observed in one such 3D frame (based on echo ultrasound images and/or Doppler color images).

In step 130, a dynamic jet is segmented from the time sequence of stabilized 3D ultrasound images. The jet segmentation uses mathematical morphology, and may include an averaging over the whole sequence of 3D ultrasound images for smoothing.

The mathematical morphology may be used to estimate the average orientation of the jet over time (i.e. over frames of the time sequence of 3D ultrasound images). This may guide the search for the orifice for each image independently. The averaging may also refer to performing an averaging of the shape of the jet over the time sequence of 3D ultrasound images.

In step 140, a dynamic surface model is fit to the valve based on the segmented dynamic jet.

The fitting of the surface model may include applying an analytic geometric regression to the segmented jet from step 130. The algorithm locates the valve, such as a mitral valve, along the previously found jet directions, as determined by the segmentation, and may use analytic geometric regression to fit a surface model. The surface model may be visualized as a mesh.

In step 150, a dynamic regurgitant orifice is identified based on the dynamic surface model and the time sequence of stabilized 3D ultrasound images.

In the 4D ultrasound Doppler color data, a search is performed through the volume along the valve surface, as defined by the dynamic surface model, to identify one or more regurgitant orifices.

In step 160, a flow convergence model is fit to the time sequence of stabilized 3D ultrasound images based on the identified dynamic regurgitant orifice. This step may help refine the identification and localization of the orifice.

The identified regurgitant orifice may be used to fit a flow convergence model to the time sequence of stabilized 3D ultrasound images. The flow convergence model may be visualized, for example, as a wireframe object.

In step 170, a regurgitant flow is estimated based on the identified regurgitant orifice and time sequence of stabilized 3D ultrasound images.

In this way several orifices, or a complex orifice with various shapes (such as slit orifice), may be handled by the method. Thus, the method may be applied to a variety of use cases for which valve regurgitation assessment needs to be made, and is not tied to the pinhole orifice assumption that is made in the state-of-the-art PISA method.

The direct estimation of regurgitant flow values derives from the orifice surface model and flow convergence data. This may be repeated for each frame, and the regurgitant flow integrated over the frames of a cardiac cycle to determine the regurgitant volume.

Further, the estimated regurgitant flow values, which may include regurgitation flow curves and an integrated regurgitant volume value, may be provided to a user.

Figure 3A:
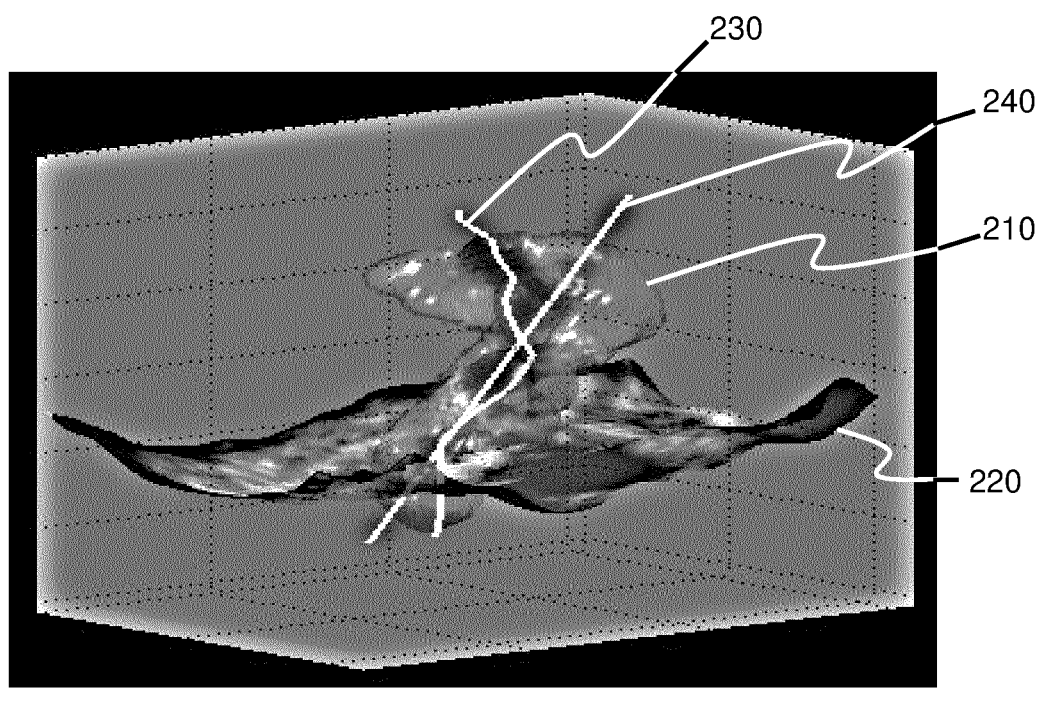
FIGS. 3a to 3c show visualizations of some of the method steps of FIG. 2.
Figure 3B:
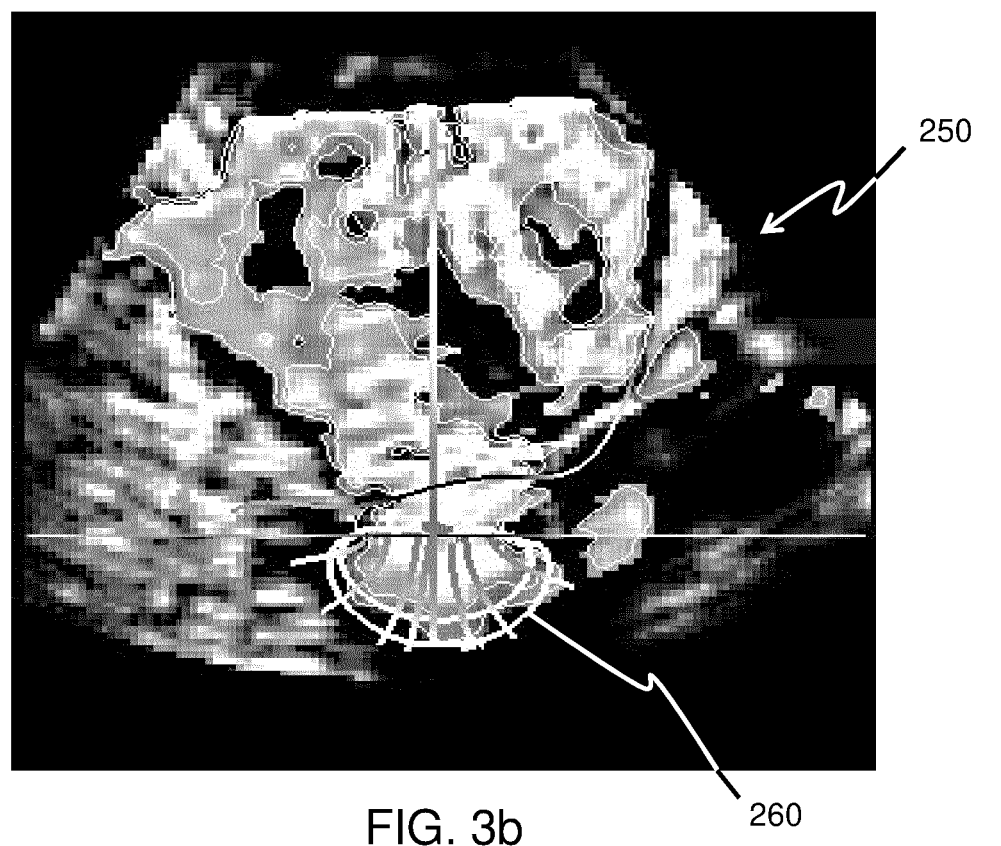
Figure 3C:
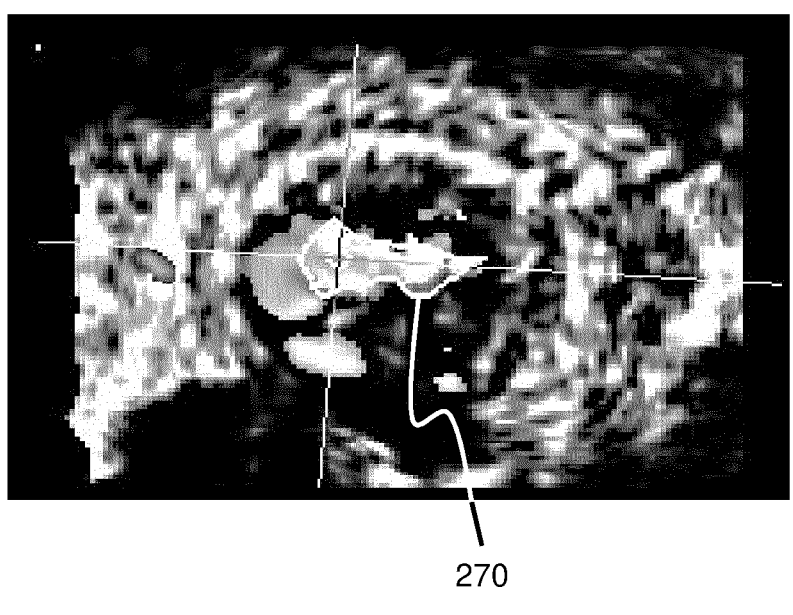

FIGS. 3a to 3c show an illustrative example (applied to TEE data) showing the visualized outputs from the method described above with reference to FIG. 2, on one frame of the time sequence of 3D ultrasound frames.

FIG. 3a shows a segmented jet 210 in proximity to a valve surface 220 with an estimated jet centerline 230 and jet axis 240. FIG. 3b shows a 2D view of a valve surface model 250 with a fitted flow convergence model 260. FIG. 3c shows a segmented orifice 270 within a B-mode ultrasound image frame.

The invention is of particular interest for mitral regurgitation quantification from TEE or TTE 4D color data. It may however also be used for mitral inflow quantification, aortic outflow quantification, and indeed for analysis of other valves.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A method for calculating cardiac valve regurgitation, the method comprising:

obtaining four-dimensional (4D) ultrasound data of a region of interest, wherein the region of interest comprises a cardiac valve and wherein the 4D ultrasound data comprises a time sequence of three-dimensional (3D) ultrasound images comprising B-mode ultrasound data and color Doppler ultrasound data;

performing image stabilization on the images of the time sequence of 3D ultrasound images;

segmenting a dynamic jet from the time sequence of stabilized 3D ultrasound images, wherein the segmenting of the dynamic jet comprises determining a jet direction;

fitting a dynamic surface model to the 4D ultrasound data of the cardiac valve in the time sequence of stabilized 3D ultrasound images using the segmented dynamic jet and the jet direction;

identifying a dynamic regurgitant orifice based on the dynamic surface model and the time sequence of stabilized 3D ultrasound images;

fitting a flow convergence model to the time sequence of stabilized 3D ultrasound images based on the dynamic regurgitant orifice; and estimating a regurgitant flow value based on the time sequence of stabilized 3D ultrasound images.

2. The method as claimed in claim 1, wherein the method further comprises receiving a user input, wherein the user input comprises one or more of:

selecting one or more 3D ultrasound images of the time sequence of stabilized 3D ultrasound images; and selecting an orifice within the one or more 3D ultrasound images.

3. The method as claimed in claim 1, wherein the performing of the image stabilization comprises applying a sparse optical flow method to the time sequence of stabilized 3D ultrasound images fast image stabilization.

4. The method as claimed in claim 1, wherein the performing of the image stabilization comprises applying a point selection routine to the time sequence of stabilized 3D ultrasound images.

5. The method as claimed in claim 1, wherein the performing of the image stabilization comprises performing a trajectory analysis on the time sequence of stabilized 3D ultrasound images, wherein the trajectory analysis comprises an anti-drifting mechanism.

6. The method as claimed in claim 1, wherein the segmenting of the dynamic jet comprises averaging over the time sequence of stabilized 3D ultrasound images.

7. The method as claimed in claim 6, wherein the averaging comprises estimating a jet centerline of the segmented dynamic jet over the time sequence of stabilized 3D ultrasound images.

8. The method as claimed in claim 6, wherein the averaging comprises averaging an orientation of the segmented dynamic jet over the time sequence of stabilized 3D ultrasound images.

9. The method as claimed in claim 1, wherein the fitting of the dynamic surface model comprises analytic geometric regression.

10. The method of claim 1, wherein the identifying of the dynamic regurgitant orifice comprises segmenting the dynamic regurgitant orifice based on the dynamic surface model and the time sequence of stabilized 3D ultrasound images.

11. The method of claim 1, wherein the method further comprises estimating a regurgitant volume based on an integration of the estimated regurgitant flow value over time.

12. A non-transitory computer-readable medium having stored thereon a computer program comprising instructions which, in response to said computer program is executed by a processor cause the processor to carry out the method of claim 1.

13. A computer system comprising a processor, wherein the processor is adapted to:

obtain four-dimensional (4D) ultrasound data of a region of interest, wherein the region of interest comprises a cardiac valve and wherein the 4D ultrasound data comprises a time sequence of three-dimensional (3D) ultrasound images comprising B-mode ultrasound data and color Doppler ultrasound data;

perform image stabilization on the images of the time sequence of 3D ultrasound images, segment a dynamic jet from the time sequence of stabilized 3D ultrasound images, wherein the segmenting of the dynamic jet comprises determining a jet direction:

fit a dynamic surface model to the 4D ultrasound data of the cardiac valve in the time sequence of stabilized 3D ultrasound images, using the segmented dynamic jet and the jet direction;

identify a dynamic regurgitant orifice based on the dynamic surface model and the time sequence of stabilized 3D ultrasound images;

fit a flow convergence model to the time sequence of stabilized 3D ultrasound images based on the dynamic regurgitant orifice; and estimate a regurgitant flow value based on the time sequence of stabilized 3D ultrasound images.

14. An ultrasound system, the system comprising:

an ultrasound probe adapted to acquire four-dimensional (4D) ultrasound data;

a processor, wherein the processor is adapted to:

obtain ultrasound data of a region of interest, wherein the region of interest comprises a cardiac valve and wherein the 4D ultrasound data comprises a time sequence of three-dimensional (3D) ultrasound images comprising B-mode ultrasound data and color Doppler ultrasound data;

perform image stabilization on the images of the time sequence of 3D ultrasound images;

segment a dynamic jet from the time sequence of stabilized 3D ultrasound images, wherein the segmenting of the dynamic jet comprises determining a jet direction;

fit a dynamic surface model to the 4D ultrasound data of the cardiac valve in the time sequence of stabilized 3D ultrasound images, using the segmented dynamic jet and the jet direction;

identify a dynamic regurgitant orifice based on the dynamic surface model and the time sequence of stabilized 3D ultrasound images;

fit a flow convergence model to the time sequence of stabilized 3D ultrasound images based on the dynamic regurgitant orifice; and estimate a regurgitant flow value based on the time sequence of stabilized 3D ultrasound images; and an image display configured to display one or more 3D ultrasound images of the time sequence of stabilized 3D ultrasound images.

15. The ultrasound system as claimed in claim 14, wherein the ultrasound system further comprises a user interface adapted to receive a user input, wherein the user input comprises one or more of:

selecting the one or more 3D ultrasound images of the time sequence of stabilized 3D ultrasound images; and selecting an orifice within the one or more 3D ultrasound images.

16. The system of claim 14, further comprising an image processor configured to remove one or more imaging artifacts.

17. The system of claim 16, wherein the one or more imaging artifacts comprise one or more of acoustic shadowing, posterior enhancement, reverberation artifacts, or speckle reduction.

18. The system of claim 14, further comprising a graphics processor configured to generate graphic overlays for display with the one or more 3D ultrasound images.

19. The system of claim 14, wherein the image display is further configured to display stabilized cardiac valve visualization and graphical segmentations.

20. The system of claim 14, wherein the image display is further configured to display the flow convergence model as a wireframe object.

* * * * *